United States Patent [19]

Asahina

[11] Patent Number: 5,090,038

[45] Date of Patent: Feb. 18, 1992

[54] STEREOSCOPIC X-RAY APPARATUS

[75] Inventor: Hiroshi Asahina, Tochigi, Japan

[73] Assignee: Kabushiki Kaisha Toshiba, Kawasaki, Japan

[21] Appl. No.: 592,375

[22] Filed: Oct. 3, 1990

[30] Foreign Application Priority Data

Oct. 9, 1989 [JP] Japan ................. 1-262060

[51] Int. Cl.$^5$ .............................. A61B 6/02
[52] U.S. Cl. ........................ 378/41; 378/62; 378/99
[58] Field of Search .............. 378/41, 42, 62, 99, 378/15, 4; 358/111

[56] References Cited

U.S. PATENT DOCUMENTS

4,214,267  7/1980  Roese et al. ..................... 378/99
4,769,701  9/1988  Sklebitz et al. .................. 378/41

Primary Examiner—Janice A. Howell
Assistant Examiner—David P. Porta
Attorney, Agent, or Firm—Finnegan, Henderson, Farabow, Garrett, and Dunner

[57] ABSTRACT

Pulsed X-rays are emitted to a subject under examination at regular intervals while an arm supporting an X-ray tube and a combination of an image intensifier tube and a TV camera so as to interpose the subject therebetween is rotated around the subject at a given speed, thereby obtaining a number of X-ray images of the subject at intervals of a constant angle of view. The X-ray images are converted to optical images which are taken by the TV camera to obtain image signals. Image signals are stored in respective frame memories. Two image signals with an interval of a predetermined number of frames are read from the frame memories and displayed on right and left display screens. The displayed images are viewed by an observer through a stereoscopic viewer for guiding the right and left images to the right and left eyes of the observer, respectively. The frame interval between the two images is selected such that the displayed images have a predetermined difference in angle of view which will give the observer a desired sensation of stereoscopy. Even if only the two images are displayed statically or even if pairs of such two images are displayed dynamically, therefore, stereoscopic presentation of images of the subject can be made.

26 Claims, 7 Drawing Sheets

STEREOSCOPIC X-RAY APPARATUS

BACKGROUND OF THE INVENTION

1. Field of the Invention

The present invention relates to a stereoscopic X-ray apparatus which permits stereoscopic observation of a subject under examination using a number of X-ray images of the subject obtained by emitting X-rays from an X-ray tube to the subject from many directions and at regular intervals while rotating the X-ray tube around the subject.

2. Description of the Related Art

According to a conventional stereoscopic X-ray apparatus, an X-ray tube and an image intensifier are supported by a C-shaped arm, and the arm is rotated so that the X-ray tube and the image intensifier rotate around a subject under examination, during which time X-ray pulses are emitted to the subject periodically to obtain X-ray images of the subject from many directions. The obtained X-ray images are observed continuously. Means for obtaining the X-ray images includes means for taking optical images produced by the image intensifier by use of a movie camera and means for taking the images by use of a television camera.

With the prior art, the continuous observation of many X-ray images which vary continuously in the direction of line of view causes an observer to imagine as if he or she rotated around the subject under examination continuously thus permitting stereoscopic vision of images of the subject. It is therefore required to always change the direction of line of view of the X-ray images. With the continuous observation of only one X-ray image, stereoscopic vision is impossible. The static image presentation for careful observation of the subject for diagnosis will provide no sensation of stereoscopy. Because the stereoscopic vision depends to a large extent on the human sensibilities, the degree of the sensation of stereoscopy acquired will differ from person to person. For this reason, some people may recognize an actual distance relationship between two objects erroneously. Furthermore, the sensation of stereoscopy is related to display speed for continuous observation, thus involving much difficulty in achieving the optimum sensation of stereoscopy.

SUMMARY OF THE INVENTION

It is an object of the present invention to provide a stereoscopic X-ray apparatus which permits an observer to have a sensation of stereoscopy even for static display.

It is another object of the present invention to provide a stereoscopic X-ray apparatus which permits the degree of a sensation of stereoscopy to be changed and any person to recognize the distance relationship between two objects correctly.

According to the present invention, there is provided a stereoscopic X-ray apparatus comprising X-ray image taking means for emitting X-rays to a subject under examination from a number of directions while rotating around the subject and taking a number of X-ray images of the subject, storage means for storing the X-ray images output from the X-ray image taking means, and stereoscopic display means for reading two X-ray images with a predetermined difference in the direction of emission of X-rays from the storage means and visually displaying them.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention, and in which.

DETAILED DESCRIPTION OF THE PREFERRED EMBODIMENTS

Figure 1:
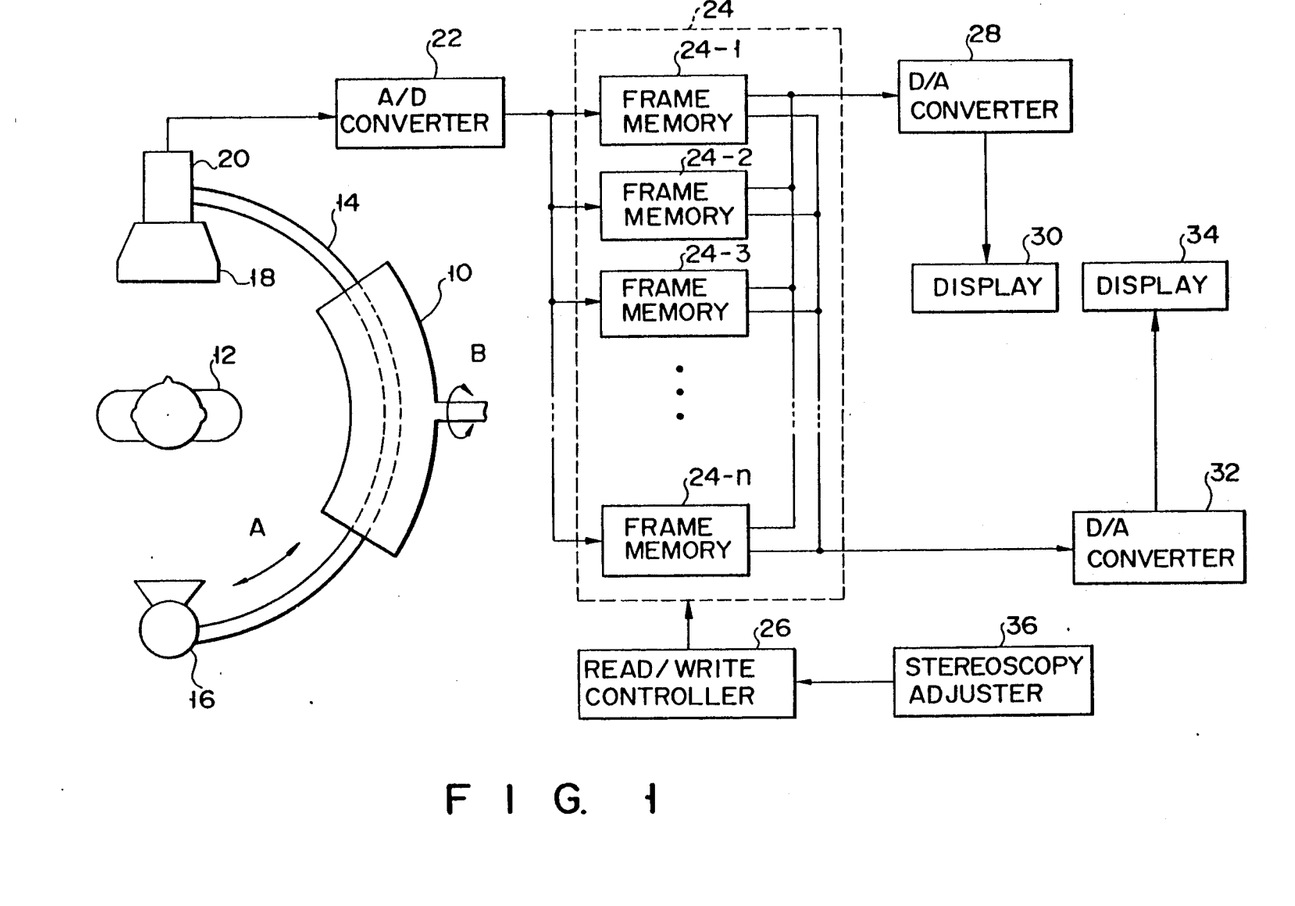
FIG. 1 is a block diagram of a stereoscopic X-ray apparatus according to a first embodiment of the present invention.

Preferred embodiments of a stereoscopic X-ray apparatus according to the present invention will be described with reference to the accompanying drawings. Referring now to FIG. 1, which is a block diagram of a first embodiment, an arm 14 is provided which is moved in the direction of an arrow A along a circle centered at the body axis of a subject 12 under examination lying on an examination couch not shown by a motor (not shown) installed within an arm holder 10 mounted on the X-ray apparatus main body (not shown). The arm 14, which is substantially semicircular, is provided with an X-ray tube 16 attached to its one end and a combination of an image intensifier tube 18 and a TV camera 20 attached to its other end. For this reason, when the arm 14 moves in the direction of the arrow A, the X-ray tube 16 rotates around the subject 12 transversely with the body axis of the subject 12 taken as the center. When the arm 14 moves at a predetermined speed and the X-ray tube 16 emits pulsed X-rays at regular intervals, the subject 12 is irradiated with X-rays from many directions at intervals of a constant angle, thereby obtaining X-ray images viewed from many directions. The arm 14 is not required to rotate around the subject 12 fully but has only to move so that X-rays may be emitted to the subject 12 from at least two directions. However, although X-ray images taken from two directions may suffice in the case of static image presentation, X-ray images taken from many directions are needed for dynamic image presentation.

The arm holder 10 is rotatable as shown by an arrow B with a straight line, which is in a plane parallel to the couch and perpendicular to the body axis of the subject 12, taken as its rotation axis. Such rotation of the arm 10 permits the X-ray tube 16 to rotate around the subject 12 in a cranio-caudal direction along its body axis. The cranio-caudal rotation is not related to the first embodiment of the present invention but used in a second embodiment of the present invention.

An X-ray image incident on the image intensifier tube 18 is converted into an optical image and then picked up by the TV camera 20. An image signal from the TV camera 20 is stored into an image memory 24 via an A/D converter 22. The image memory 24 comprises number of frame memories 24-1 to 24-n in which n number of X-ray images taken at intervals of a given angle are stored in sequence. The value for n, the given angle relating to the period of emission of X-rays, and the moving speed of the arm 14 are determined properly. An output signal of the image memory 24 is applied to a display section 30 via a D/A converter 28 and also to a display section 34 via a D/A converter 32. The display sections 30 and 34 are placed in parallel and adjacent to each other The read and write operations for the memory 24 are controlled by a read/write controller 26. The present embodiment is arranged to permit the degree of sensation of stereoscopy to be changed and thus is provided with a stereoscopy adjuster 36 which is connected to the read/write controller 26. The adjuster 26 will be described later in detail.

Figure 2:
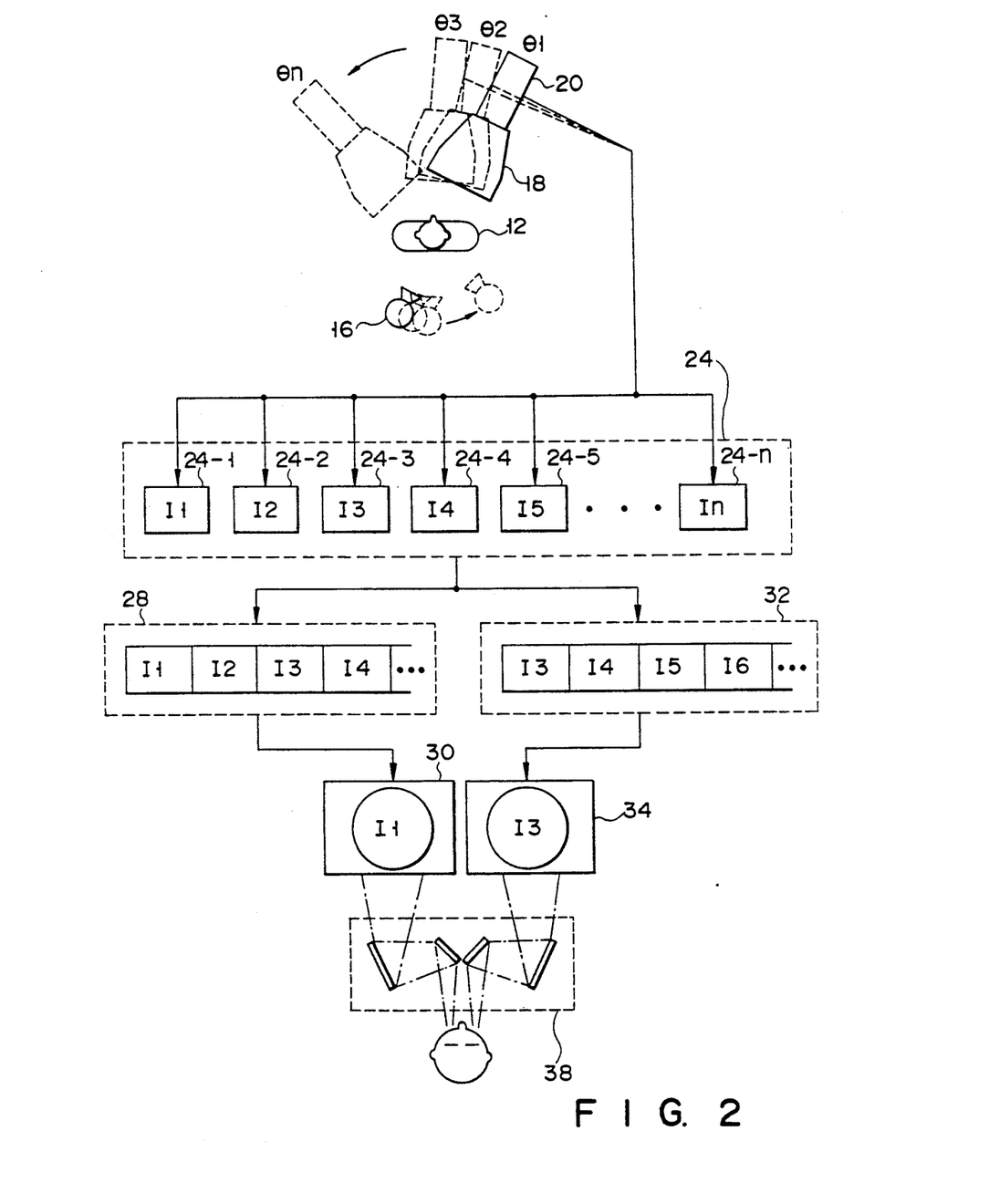
FIG. 2 is a diagram for use in explanation of the operation of the first embodiment.

The operation of the first embodiment will be described with reference to FIG. 2. First, with the memory 24 set in write mode, pulsed X-rays are emitted at regular intervals while the arm 14 is moved at a given speed. When the image intensifier tube 18 (or the X-ray tube 16) arrives at points in its orbit at which the subject is viewed from angles $\theta 1, \theta 2, ..., \theta n$, pulsed X-rays are emitted to obtain X-ray images I1, I2, ..., In which correspond to the angles $\theta 1, \theta 2, ..., \theta n$, respectivey. The X-ray images I1, I2, ... In are stored in the frame memories 24-1, 24-2,..., 24-n in the order in which they are taken. If the moving speed of the arm 14 is constant, the angle of view ($\theta 1, \theta 2, ..., \theta n$) is changed by increments of $\delta$. That is, any two successive images I1 and I2; I2 and I3; ...; In-1 and In have a difference of $\delta$ in angle of view.

Next, the controller 26 sets the memory 24 in read mode (at this time the subject 12 may stay away from the apparatus) so as to read image data from the frame memories 24-1, 24-2, ..., 24-n in the order in which they are taken and synchronously with the frame period of the display sections 30 and 34. The read-out image data are displayed on the left display section 30 after being converted to analog signals by the D/A converter 28. The image data may again be read from the frame memory 24-1 after the image data has been read from the frame memory 24-n so as to repeat reading of images. A predetermined image data is read from the image memory 24 for display on the right display section 34 synchronously with the data readout for display on the left display section 30. Two images taken from different angles of view are selected herein for stereoscopic vision. To this end, the controller 26 sequentially reads from the memory 24 images, which are displaced from X-ray images which are being displayed dynamically on the left display section 30 by a predetermined number of frames, for application to the right display section 34 via the D/A converter 32. The interval of two frames which are displayed on both display sections 30 and 34 is specified by the stereoscopy adjuster 36. In the present embodiment, let the interval of frames be two frames. Therefore, X-ray images I1, I2, I3, ... are sequentially applied to the D/A converter 28 and X-ray images I3, I4, I5, ... are sequentially applied to the D/A converter 32 so that pairs of images with an angular difference of 2$\delta$ are displayed dynamically on the left and right display sections 30 and 34.

According to the first embodiment, as described above, X-ray images are taken from different angles spaced at regular angular intervals while the X-ray tube 16 is rotated around the subject, and they are temporarily stored in the memory 24 and then read therefrom in pairs of two frames of images with a predetermined frame interval therebetween for simultaneous display on the left and right display sections 30 and 34, thereby causing parallax corresponding to the frame interval between each pair of two images viewed by two eyes of an observer and allowing the observer to view stereoscopic X-ray images of the subject. It is important here that the left and right images enter the left and right eyes of the observer, respectively. If necessary, therefore, the images on the display sections 30 and 34 may be viewed with the aid of a stereoscopic viewer 38 (refer to FIG. 2) adapted to separate the left and right images from each other. Since the parallax necessary for sensation of stereoscopy differs from person to person, the frame interval may be changed by the adjuster 36 when the sensation of stereoscopy is poor. If done so, any person may acquire better sensation of stereoscopy without fail. The adjustment therefor is very simple. In addition, since the observation of the subject is made on the basis of images reproduced from the memory 24, in order to adjust the sensation of stereoscopy it is not required to emit X-rays to the subject many times on a trial and error basis.

With the present embodiment, it is not necessarily required to display images dynamically because two images with parallax are displayed side by side. In addition, two display sections need not be provided separately. That is, the left and right halves of one display screen may be used as the display sections 30 and 34, respectively. If the images displayed on the left and right display sections will be displayed on the right and left display sections, the distance relationship between two objects in a stereoscopy is reversed. Therefore, when the moving direction of the arm 14 is reversed, the images displayed on the left and right display sections must be displayed on the right and left display sections in order to correct the distance relationship between two objects in a stereoscopy.

Figure 3:
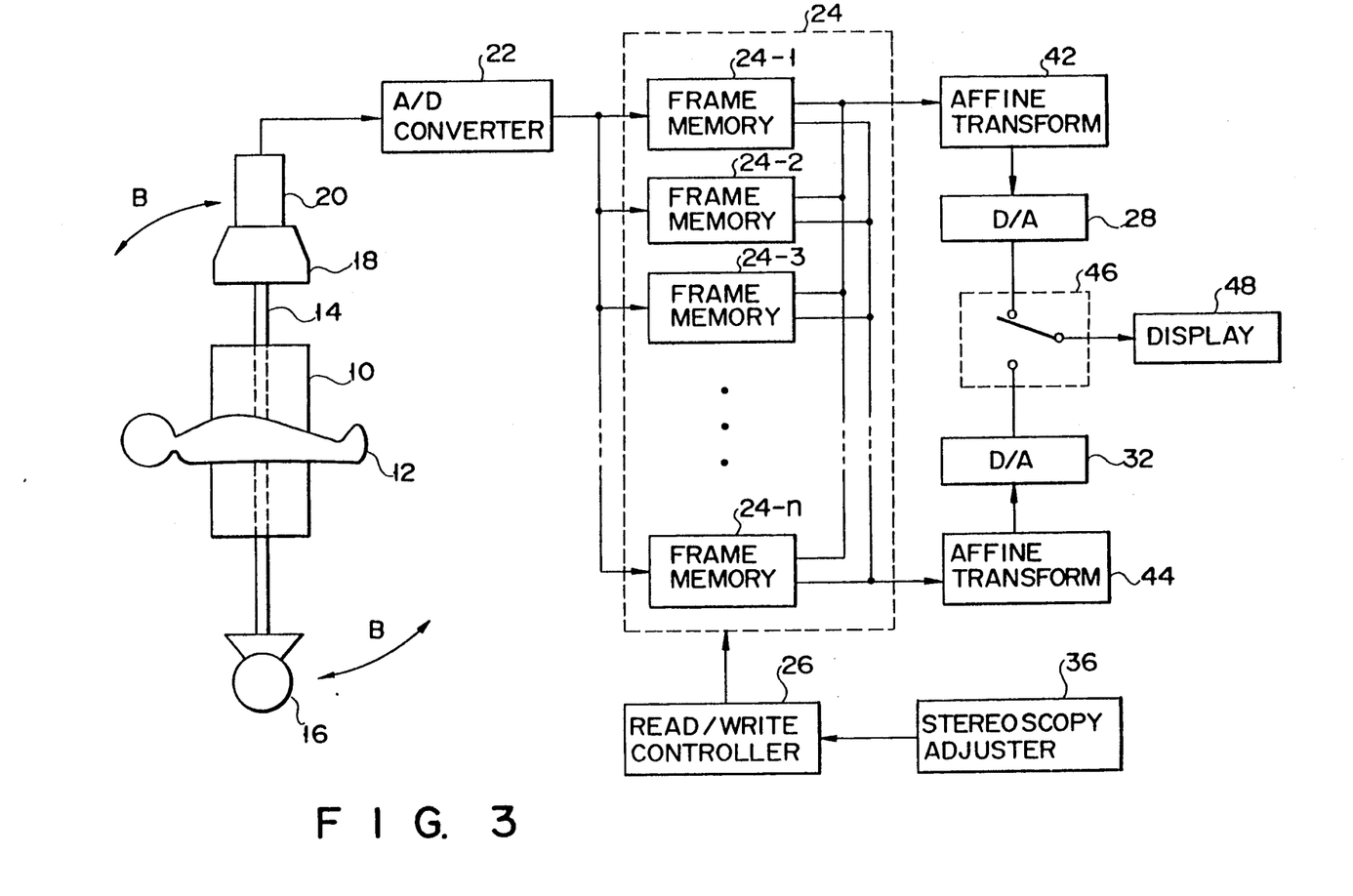
FIG. 3 is a block diagram of a stereoscopic X-ray apparatus according to a second embodiment of the present invention.

A second embodiment of the present invention will be described next. In the second embodiment, the same reference numerals are used to designate corresponding portions of the first embodiment and detailed description thereof is omitted. FIG. 3 is a block diagram of the second embodiment. The second embodiment differs from the first embodiment in the direction of rotation of the X-ray tube 16. Although, in the first embodiment, the arm 14 is rotated on the body axis of the subject 12 and the X-ray tube 16 is transversally rotated around the subject, the arm holder 10 is rotated on an axis perpendicular to the body axis of the subject 12 and the X-ray tube 16 is moved in the cranio-caudal direction of the subject in the second embodiment. Assuming that the TV camera 20 is the same as that in the first embodiment with respect to its direction, even if two images taken at an interval of predetermined frame periods are merely displayed right and left, they have parallax only in the direction of the upper and lower sides of the subject, thus failing to produce a sensation of stereoscopy. For sensation of stereoscopy, the parallax for two images must be horizontal (right and left) because human eyes are aligned horizontally (right and left).

In the second embodiment, therefore, Affine transformers 42 and 44 are connected between the image memory 24 and the D/A converters 28 and 32, which have a function of rotating an image counterclockwise through an angle of 90 degrees. Alternatively, an Affine transformer may be connected between the A/D converter 22 and the image memory 24. Although the first embodiment uses two display screens for static stereoscopic display, the second embodiment uses one display screen for dynamic stereoscopic display needing a field switcher glass with an electronic shutter as the other example of stereoscopic display. To this end, outputs of the D/A converters 28 and 32 are alternately applied to the display section 48 via a selector 46.

Figure 4:
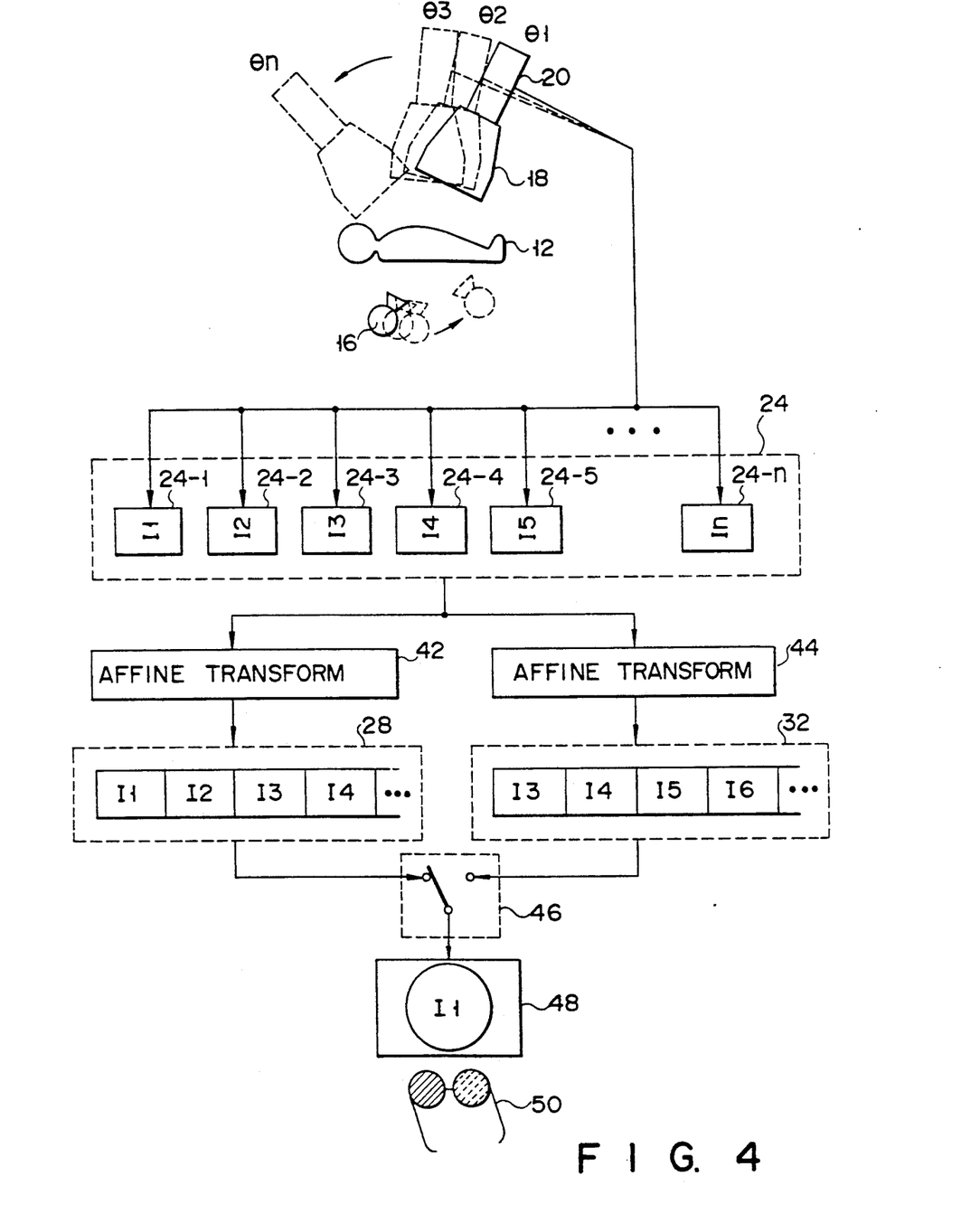
FIG. 4 is a diagram for use in explanation of the operation of the second embodiment.

The operation of the second embodiment will be described with reference to FIG. 4. The write operation for the memory 24 is the same as that in the first embodiment. The second embodiment differs from the first embodiment in that images taken from different angles which are displaced in increments of $\delta$ along the craniocaudal direction of the subject are written into frame memories 24-1, 24-2, ..., 24-n in sequence.

For this reason, image data read from the memory 24 are applied to the Affine transformers 42 and 44 so that the orientations of the images are rotated counterclockwise by 90 degrees as if frames of images taken from different angles which are displaced in increments of $\delta$ in the transverse (right-left) direction of the subject were read from the memory 24.

Supposing an input image to be f(r) (r stands for space coordinates) and the image after transformation to be g(r), the general expression for the Affine transformation for rotating an image counterclockwise by 90 degrees is given by $$g(r) = f(A^{-1})(r)$$

where $$A = \begin{bmatrix} \cos\theta & \sin\theta \\ -\sin\theta & \cos\theta \end{bmatrix}$$

From two frame memories for storing images taken at two-frame intervals are applied in sequence to the D/A converters 28 and 32 pairs of two X-ray images having a predetermined difference of $2\delta$ in viewing angle as in the first embodiment. The outputs of the D/A converters 28 and 32 are alternately applied to the display section 48 via the selector 46 for alternate display of paired images. The left and right shutters of the field switcher glass 50 ar closed and opened synchronously with the alternate display. For example, when the output of the D/A converter 28 is displayed, the right shutter is closed, while the left shutter is opened so that the displayed image is viewed by the left eye of the observer. This causes parallax between the two images viewed by both eyes of the observer a in the first embodiment, thus allowing the observer to view a stereoscopic X-ray image of the subject. It is to be noted that the parallax can easily be varied by the use of the stereoscopy adjuster 36. In addition, in the second embodiment, the read-out period cycle of the memory 24 is twice that in the first embodiment because two images are alternately displayed on a single display screen.

In the second embodiment as well, if only a pair of two images with parallax is displayed alternately and repeatedly, then stereoscopic static image display will be made possible. Also, two display screens may be used as in the first embodiment. Conversely, the combined use of a single display section for alternate display and a field switcher glass may also be made in the first embodiment.

If the orientation of the TV camera 20 itself or the display section 48 itself can be changed by 90 degrees in the case where the X-ray tube 16 is moved in the craniocaudal direction of the subject as in the second embodiment, there will be no need for the Affine transformation. For rotation of image data, similar techniques other than the Affine transformation may be used.

Figure 5:
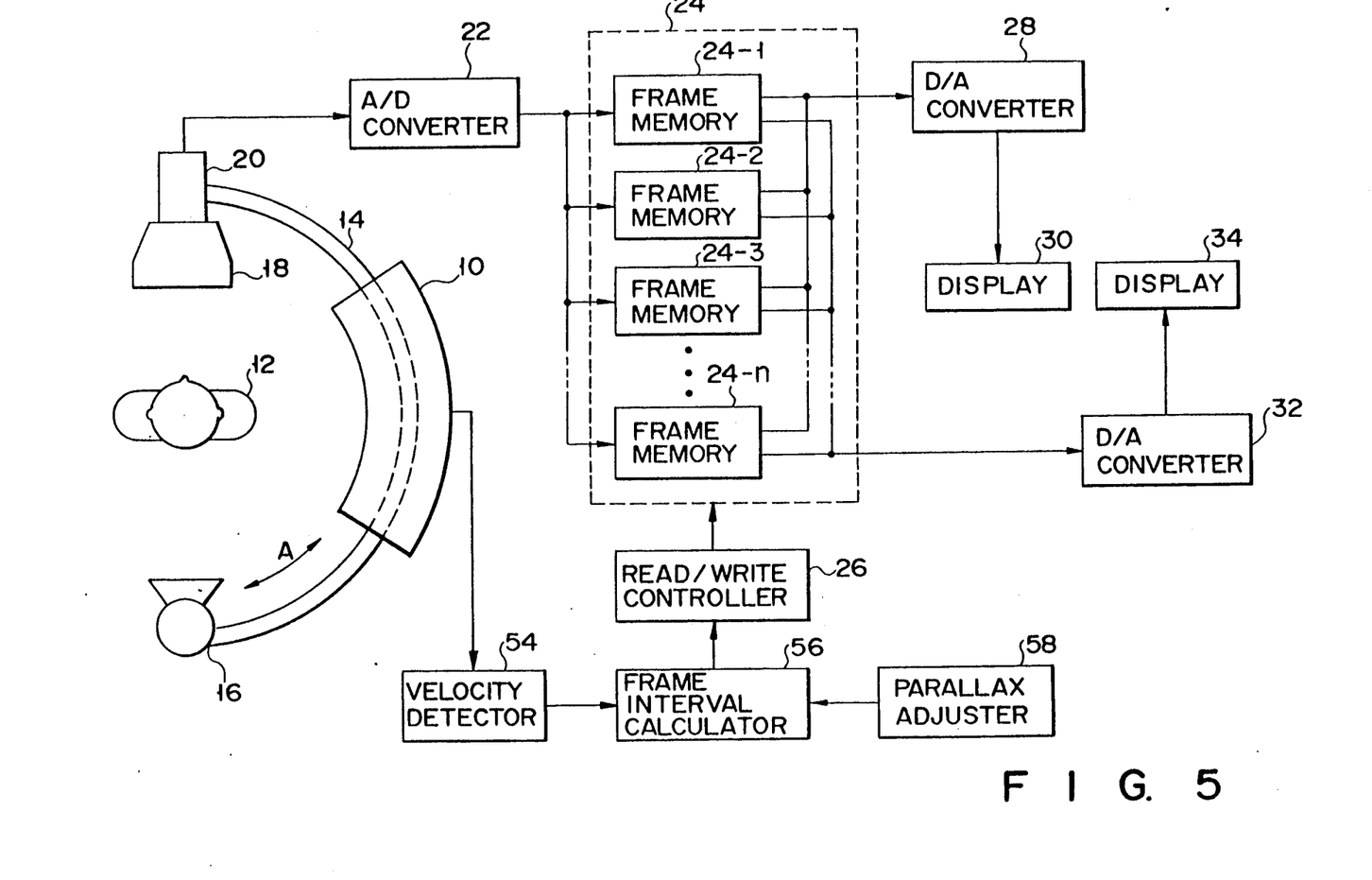
FIG. 5 is a block diagram of a stereoscopic X-ray apparatus according to a third embodiment of the present invention.

FIG. 5 is a block diagram of a third embodiment of the present invention. The third embodiment is distinct from the first embodiment in that a velocity detector 54 for detecting the moving speed of the arm 14 and the rotating speed of the arm holder 10 and a frame interval calculator 56 are added and a parallax adjuster 58 for specifying parallax between two images for stereoscopic display is provided in place of the stereoscopy adjuster 36 for specifying a frame interval. That is, in the above embodiments, a pair of X-ray images with a given frame interval therebetween are used for stereoscopic vision on the assumption that the moving speed of the X-ray tube 16 relative to the subject 12 is constant and the angular distance between angles of view for successive frames is constant. If, therefore, the moving speed of the arm 14 or the rotational speed of the arm holder 10 is not uniform, a variation will occur in parallax of two images, providing varying sensation of stereoscopy. In the present embodiment, therefore, the moving speed of the arm 14 and the rotational speed of the arm holder 10 are detected and a frame interval corresponding to the detected travel speed, rotational speed, and parallax specified from the parallax adjuster 58 is calculated by the calculator 56, which is entered into the read/write controller 26. The controller 26 reads two images from two frame memories corresponding to the calculated frame interval.

Figure 6:
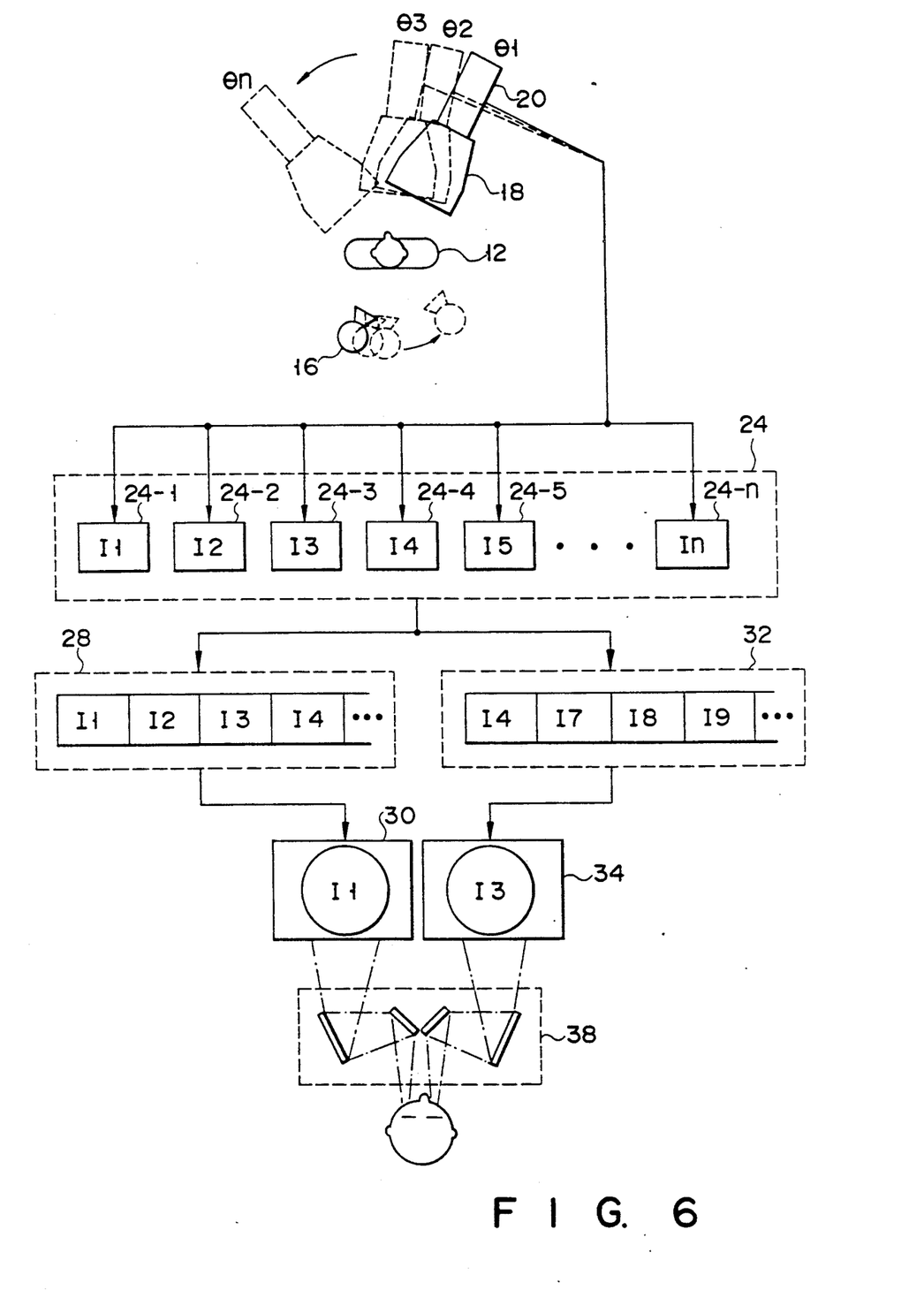
FIG. 6 is a diagram for use in explanation of the operation of the third embodiment.
Figure 7:
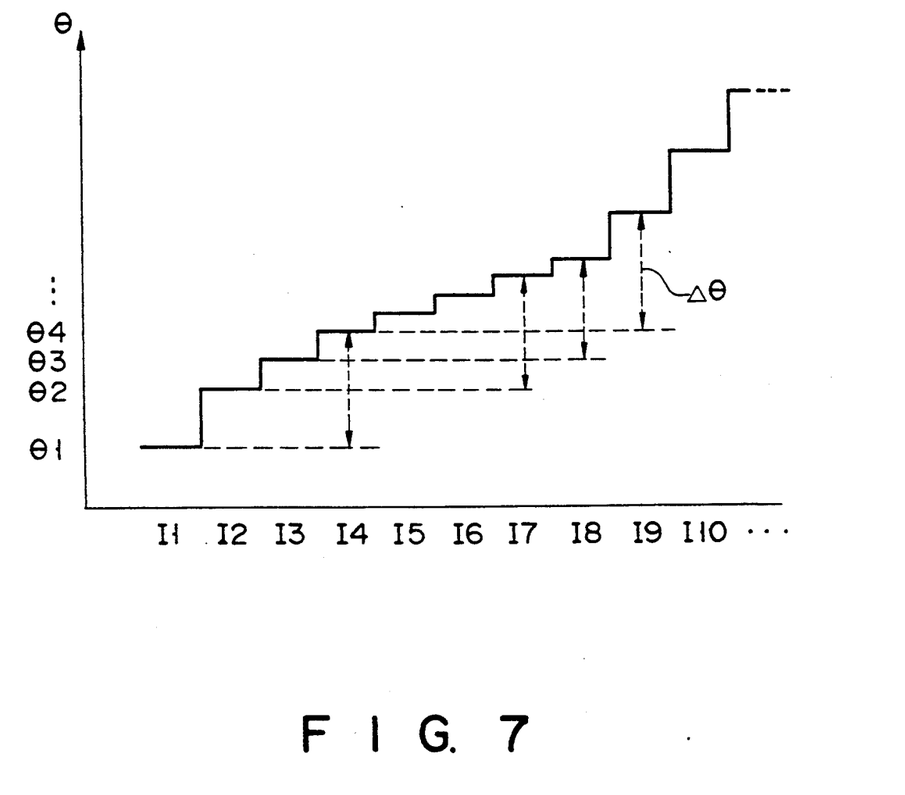
FIG. 7 is a diagram illustrating a relationship between X-ray images and directions of view in the third embodiment.

The operation of the third embodiment will be described with reference to FIGS. 6 and 7. As illustrated in FIG. 6, pulsed X-rays are emitted at regular intervals while the arm 14 is moved. Thereby, X-ray images are obtained at viewing angles $\theta_1$, $\theta_2$, ..., $\theta_n$ and then entered into the frame memories 24-1, 24-2,..., 24-n in sequence. Since the travel speed of the arm 14 is not uniform herein, the viewing angles of the X-ray images written into the frame memories have unequal intervals as illustrated in FIG. 7. The viewing angles $\theta_1$, $\theta_2$, ..., $\theta_n$ are obtained from the moving speed of the arm 14 and the cycle of X-ray emission (which can be made constant) by the velocity detector 54. The frame interval calculator 56 obtains X-ray images (frame intervals), each of which is displaced from a respective corresponding one of X-ray images I1, I2, ..., In by a desired amount of parallax $\Delta\theta$ in viewing angle, from the viewing angles $\theta_1$, $\theta_2$, ..., $\theta_n$ and the desired amount of parallax $\Delta\theta$ input from the parallax adjuster 58. The controller 26 supplies X-ray images from the frame memories 24-1, 24-2, ..., 24-n to the D/A converter 28 in sequence and supplies X-ray images separated from the X-ray images supplied to the D/A converter 28 by the frame interval calculated by the frame interval calculator 56 to the D/A converter 32 in sequence.

Thus, even if the rotational speed of the X-ray tube 16 is not uniform, two images with a difference of $\Delta\theta$ in viewing angle are always displayed on the right and left display sections 30 and 34, thereby allowing the observer to view the stereoscopic X-ray images of the subject in a stable manner. In the present embodiment as well, the combined use of a single display and a field switcher glass may be made and the static image display may be performed. Furthermore, where the X-ray tube 16 rotates in the cranio-caudal direction of the subject, it is required to connect Affine transformers to the output of the memory 24 as is the case with the second embodiment.

According to the present invention, as described above, a stereoscopic X-ray apparatus can be provided which can obtain a sensation of stereoscopy even from a static image display, the apparatus comprising image-taking means for taking many X-ray images of a subject under examination while rotating around the subject to emit to it X-rays from many directions, storage means for storing many X-ray images taken by the image-taking means, and stereoscopic display means for reading two X-ray images with a predetermined difference in the direction of emission of X-rays from the storage means to display them. The difference in the direction of emission of X-rays in the two X-ray images may be varied to vary the degree of sensation of stereoscopy, thus providing a stereoscopy X-ray apparatus which allows any person to correctly recognize the far and near relationship between two objects.

The present invention is not limited to the above embodiments described above and may be modified in various ways. For example, X-ray images may be filmed by a movie camera instead of using a TV camera. In this case, two movie films are projected synchronously at an interval of two frames. Even if image data is used, an output optical image of an image intensifier may be taken on a film instead of using a TV camera and the image on the film may be read by an image reader for conversion to image data which is entered into a memory. As an X-ray tube, a two-focus stereoscopic X-ray tube may be used. Although, in the drawings, X-rays are emitted from the underside of the subject, they may be emitted from above. In addition, the shape of the arm for supporting the X-ray tube and the image intensifier need not be limited to the shape illustrated in the Figures.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A stereoscopic X-ray apparatus comprising:
   X-ray image taking means for emitting X-rays to a subject under examination from plural directions while moving around the subject and taking plural X-ray images of the subject;
   storage means for storing said X-ray images taken by said X-ray image taking means, said storage means including first to nth memories for storing first to nth X-ray images in the order in which they are taken, respectively; and
   stereoscopic display means for reading two X-ray images with a predetermined difference in the direction of emission of X-rays from said storage means and visually displaying the two X-ray images, said stereoscopic display means including means for reading the X-ray images from said first to nth memories in sequence and the X-ray images from said memories following the (i-1)th memory in sequence and synchronously with reading from said first to nth memories (where i stands for a positive integer corresponding to the predetermined difference).

2. An apparatus according to claim 1, wherein said stereoscopic display means includes means for varying said difference.

3. An apparatus according to claim 1, wherein said stereoscopic display means includes means for displaying said two X-ray images statically.

4. An apparatus according to claim 3, wherein said stereoscopic display means includes means for displaying said two X-ray images alternately.

5. An apparatus according to claim 4, further comprising a viewing aid adapted for use by an observer and having shutters for permitting images to enter the right and left eyes of the observer alternately in synchronism with the alternate display of said stereoscopic display means.

6. An apparatus according to claim 1, wherein said stereoscopic display means includes means for displaying said two X-ray images side by side simultaneously.

7. An apparatus according to claim 6, further comprising a viewing aid adapted for use by an observer for guiding said right and left images to the right and left eyes of the observer, respectively.

8. A stereoscopic X-ray apparatus comprising:
   X-ray image taking means for emitting X-rays to a subject under examination from plural directions while moving around the subject and taking plural X-ray images of the subject;
   storage means for storing said X-ray images taken by said X-ray image taking means; and
   stereoscopic display means for reading two X-ray images with a predetermined difference in the direction of emission of X-rays from said storage means and visually displaying the two X-ray images, said stereoscopic display means including first means for continuously displaying a number of X-ray images in the order in which they are taken and second means for displaying X-ray images, each of which has a predetermined difference in the direction of emission of X-rays with respect to a respective individual one of the X-ray images which is being displayed by said first means.

9. An apparatus according to claim 8, wherein said stereoscopic display means includes means for varying said difference.

10. An apparatus according to claim 8, wherein said stereoscopic display means includes means for displaying said X-ray images alternately.

11. An apparatus according to claim 10, further comprising a viewing aid adapted for use by an observer and having shutters for permitting images to enter the right and left eyes of the observer alternately in synchronism with the alternate display of said stereoscopic display means.

12. An apparatus according to claim 8, wherein said stereoscopic display means includes means for displaying said two X-ray images side by side simultaneously.

13. An apparatus according to claim 12, further comprising a viewing aid adapted for use by an observer for guiding said right and left images to the right and left eyes of the observer, respectively.

14. An apparatus according to claim 8, wherein said stereoscopic display means includes means for displaying said two X-ray images statically.

15. A stereoscopic X-ray apparatus comprising:
a source of X-rays for emitting pulsed X-rays to a subject under examination at regular intervals;
an image intensifier for converting an X-ray image resulting from transmission of the pulsed X-rays emitted from said source of X-rays through said subject to an optical image;
a camera coupled to said image intensifier for taking said optical image output from said image intensifier and output image data;
arm means for supporting said source of X-rays, said image intensifier, and said camera so as to interpose said subject among said source of X-rays and image intensifier and varying the direction of emission of pulsed X-rays to said subject continuously;
memory means for storing a number of frames of image data output from said camera and representing X-ray images of said subject taken from a number of directions;
readout means for reading a first sequence of frames of image data and a second sequence of frames of image data simultaneously from said memory means in the order in which they are taken, corresponding frames of image data in said first and second sequences being read at an interval of a predetermined number of frames; and
display means for providing stereoscopic presentation of X-ray images of said subject using said first and second sequences of frames of image data read from said memory means by said readout means.

16. An apparatus according to claim 15, wherein said arm means includes means for varying the direction of emission of pulsed X-rays to said subject so that the field of view of said camera may vary along the transversal direction of said subject.

17. An apparatus according to claim 15, wherein said arm means includes means for varying the direction of emission of pulsed X-rays to said subject so that the field of view of said camera may vary along the craniocaudal direction of said subject, and which further comprises means for rotating the image data by 90 degrees.

18. An apparatus according to claim 17, wherein said image data rotating means includes an Affine transforming circuit for rotating the image data read from said memory means counterclockwise by 90 degrees.

19. An apparatus according to claim 15, wherein said readout means includes means for specifying said number of frames through an operator.

20. An apparatus according to claim 15, wherein said readout means includes means for specifying a desired angle of parallax through an operator, means for detecting a speed of variation in the direction of emission of X-rays to said subject by said arm means and means for determining said number of frames in accordance with the detected speed of variation and the specified angle of parallax.

21. An apparatus according to claim 20, wherein said frame number determining means includes means for determining a smaller number of frames than a predetermined number when the speed of variation is higher than a predetermined speed and determining a larger number of frames than the predetermined number when the speed of variation is lower than the predetermined speed.

22. An apparatus according to claim 15, wherein said display means includes means for displaying said first and second sequences of frames of image data alternately.

23. An apparatus according to claim 22, further comprising a viewing aid adapted for use by an observer and having shutters for permitting images to enter the right and left eyes of the observer alternately in synchronism with the alternate display of said display means.

24. An apparatus according to claim 15, wherein said stereoscopic display means includes means for displaying said first and second sequences of frames of image data side by side simultaneously.

25. An apparatus according to claim 24, further comprising a viewing aid adapted for use by an observer for guiding said right and left images to the right and left eyes of the observer, respectively.

26. An apparatus according to claim 15, wherein said display means includes means for displaying said first and second sequences of frames of image data statically.

* * * * *

UNITED STATES PATENT AND TRADEMARK OFFICE
CERTIFICATE OF CORRECTION

PATENT NO. : 5,090,038
DATED : February 18, 1992
INVENTOR(S) : Hiroshi Asahina

It is certified that error appears in the above-identified patent and that said Letters Patent is hereby corrected as shown below:

Claim 4, column 8, line 19, "claim 3" should read --claim 1--.

Signed and Sealed this

Twenty-fourth Day of August, 1993

Attest:

BRUCE LEHMAN

Attesting Officer          Commissioner of Patents and Trademarks